(12) United States Patent
Altman (10) Patent No.: US 6,443,949 B2
(45) Date of Patent: *Sep. 3, 2002

(54) METHOD OF DRUG DELIVERY TO INTERSTITIAL REGIONS OF THE MYOCARDIUM

(75) Inventor: Peter A. Altman, San Francisco, CA (US)

(73) Assignee: Biocardia, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/177,765

(22) Filed: Oct. 23, 1998

Related U.S. Application Data (63) Continuation-in-part of application No. 08/816,850, filed on Mar. 13, 1997, now Pat. No. 6,086,582.

(51) Int. Cl.[7] ............................................... A61B 17/20
(52) U.S. Cl. ......................................... 606/41; 604/21
(58) Field of Search ...................... 607/3, 120; 604/19, 604/27, 93, 21; 606/41

(56) References Cited

U.S. PATENT DOCUMENTS

| | | | | |
|---|---|---|---|---|
| 4,146,029 A | * | 3/1979 | Ellinwood | 128/260 |
| 4,797,285 A | | 1/1989 | Barenholz et al. | 424/450 |
| 5,190,761 A | | 3/1993 | Liburdy | 424/450 |
| 5,324,325 A | * | 6/1994 | Moaddeb | 607/120 |
| 5,527,344 A | * | 6/1996 | Arzbaecher et al. | 607/3 |
| 5,551,427 A | | 9/1996 | Altman | 128/642 |
| 5,634,895 A | * | 6/1997 | Igo et al. | 604/21 |
| 5,662,929 A | | 9/1997 | Lagace et al. | 424/450 |
| 5,681,278 A | * | 10/1997 | Igo et al. | 604/52 |
| 5,690,682 A | * | 11/1997 | Buscemi et al. | 607/3 |

OTHER PUBLICATIONS

Kibat et al., Enzymatically Activated Microencapsulated Liposomes Can Provide Pulsatile Drug Release, 4 FASEB Journal 2533 (May 1990).
Chu et al., pH Sensitive Liposomes, 4 Journal of Liposome Research 361–395 (1994).
Liu et al., Role of Cholesterol in the Stability of pH Sensitive, Large Unilamellar Liposomes Prepared by the Detergent–Dialysis Method, 981 Biochem. Biophys. L. Act., 254–60 (1989).
Miller et al., Degradation Rates of Oral Resorbable Implants (Polylactates and Polyglycolates) : Rate Modification and Changes in PLA/PFA Copolymer Ratios, II J. Biomed. Mater. Res. 711–719 (1977).
Wang et al, pH–Sensitive Immunoliposomes Mediate Target–cell–specific Delivery and Controlled Expression of a Foreign Hene in Mouse, 84 Proc. Nat. Acad. Sci. 7851 (Nov. 1987).
Putney et al., Improving Protein Therapeutics with Sustained–Release Formulations, 16 Nature Biotechnology 153–57 (Feb. 1998).
Muhlhauser et al., Safety and Efficacy of In Vivo Gene Transfer into the Porcine Heart with Replication–deficient, Recombinant Adenovirus Vectors, 3 Gene Therapy 145–153 (1996).

(List continued on next page.)

Primary Examiner—Marvin M. Lateef
Assistant Examiner—Eleni Mantis Mercader
(74) Attorney, Agent, or Firm—K. David Crockett, Esq.; Crockett & Crockett (57) ABSTRACT

A method of treating the heart and other body tissues by injecting a compound comprised of microsphere encapsulated macromolecule therapeutic agents into the myocardium, such that the microsphere size inhibits capillary transport of the compound but may permit lymphatic transport of the compound, and the compound releases therapeutic agents upon degradation of the microsphere.

20 Claims, 4 Drawing Sheets

OTHER PUBLICATIONS

March et al., Biodegradable Microspheres Containing a Colchicine Analogue Inhibit DNA Synthesis in Vascular Smooth Muscle Cells, 89 Circulation 1929–1933 (May 1994).

Arras et al., The Delivery of Angiogenic Factors to the Heart by Microsphere Therapy, 16 Nature Biotechnology (Feb. 1998).

Lazarous et al., Comparative Effects of Basic Fibroblast Growth Factor and Vascular Endothelial Growth Factor on Coronary Collateral Development and the Arterial Response to Injury, 94 Circulation 1074–1082 (Sep. 1996).

Lin et al., Expression of Recombinant Genes In Myocardium In Vivo After Direct Injection Of DNA, 82 Circulation 2217–2221 (Dec. 1990).

French el at., Direct In Vivo Gene Transfer into Porcine Myocardium using Replication Deficient Adenoviral Vectors, 90 Circulation 2414–2424 (Nov. 1994).

Miller, Lymphatics of the Heart, Raven Press, New York (1982).

Scheinman et al., Supraventricular Tachyarrhythmias: Drug Therapy Versus Catheter Ablation, 17 Clin. Cardiol. II–11 (1994).

Wang et al., Highly Efficient DNA Delivery Mediated by pH–Sensitive Immunoliposomes, 28 Biochemistry 9508 (1989).

Gerasimov, et al., Triggered Release from Liposomes Mediated by Physically and Chemically Induced Phase Transitions, Vesicles, Edited by Morton Rosoff, Marcel Dekker, Inc., New York (1996).

* cited by examiner

FIG. 4a
TIME = t1

FIG. 4b
TIME = t2

FIG. 4c
TIME = t3

FIG. 4d
TIME = t4

METHOD OF DRUG DELIVERY TO INTERSTITIAL REGIONS OF THE MYOCARDIUM

This application is a continuation in part of U.S. App. Ser. No. 08/816,850 filed Mar. 13, 1997 now U.S. Pat. No. 6,086,582.

FIELD OF THE INVENTION

The present invention relates to the interstitial delivery of particulate drug delivery systems for large and small molecule therapeutic agents within the heart.

BACKGROUND OF THE INVENTION

Local drug delivery provides many advantages. Approaches for local controlled release of agents at a depth within a tissue such as the heart, pancreas, esophagus, stomach, colon, large intestine, or other tissue structure to be accessed via a controllable catheter will deliver drugs to the sites where they are most needed, reduce the amount of drug required, increase the therapeutic index, and control the time course of agent delivery. These, in turn, improve the viability of the drugs, lower the amount (and cost) of agents, reduce systemic effects, reduce the chance of drug-drug interactions, lower the risk to patients, and allow the physician to more precisely control the effects induced. Such local delivery may mimic endogenous modes of release, and address the issues of agent toxicity and short half lives.

Local drug delivery to the heart is known. In U.S. Pat. No. 5,551,427, issued to Altman, implantable substrates for local drug delivery at a depth within the heart are described. The patent shows an implantable helically coiled injection needle which can be screwed into the heart wall and connected to an implanted drug reservoir outside the heart. This system allows injection of drugs directly into the wall of the heart acutely by injection from the proximal end, or on an ongoing basis by a proximally located implantable subcutaneous port reservoir, or pumping mechanism. The patent also describes implantable structures coated with coating which releases bioactive agents into the myocardium. This drug delivery may be performed by a number of techniques, among them infusion through a fluid pathway, and delivery from controlled release matrices at a depth within the heart. Controlled release matrices are drug polymer composites in which a pharmacological agent is dispersed throughout a pharmacologically inert polymer substrate. Sustained drug release takes place via particle dissolution and slowed diffusion through the pores of the base polymer Pending applications Ser. No. 08/8816850 by Altman and Altman, and Ser. No. 09/057,060 by Altman describes some additional techniques for delivering pharmacological agents locally to the heart. Implantable drug delivery systems, such as controlled release matrices, have been well described in the literature, as has the use of delivering particulate delivery systems or particulate drug carriers such as microcapsules, lipid emulsions, microspheres, nanocapsules, liposomes, and lipoproteins into the circulating blood. However, local delivery of such micro drug delivery systems to a depth within the myocardium using endocardial catheter delivery and epicardial injection systems have not been described, and have many advantages that have not been foreseen.

Recently, local delivery to the heart has been reported of therapeutic macromolecular biological agents by Lazarous [Circulation, 1996, 94:1074–1082.], plasmids by Lin [Circulation, 1990; 82:2217–2221], and viral vectors by French [Circulation, Vol. 90, No 5, November, 1994, 2414–2424] and Muhlhauser [Gene Therapy (1996) 3, 145–153]. March [Circulation, Vol. 89, No 5, May 1994, 1929–1933.] describe the potential for microsphere delivery to the vessels of the heart, such as to limit restenosis, and this approach has also been used for the delivery of bFGF by Arras [Margarete Arras et. al., The delivery of angiogenic factors to the heart by microshpere therapy, Nature Biotechnology, Volume 16, February 1998. These approaches for microsphere delivery obstruct flow, and will be delivered preferentially to capillary beds which are well perfused. Further, these approaches do not deliver therapeutic agents to the interstitial spaces. None of this work recognizes the potential to use particulate drug delivery system to optimize local drug delivery at a depth within the myocardium. This art also does not recognize the potential such delivery systems have in treating disease substrates in the myocardium if delivered to an appropriate region of the myocardial interstitium.

Problems exist for delivering small molecules or lipophilic molecules which rapidly transport through the capillary wall, to well-perfused tissues such as the myocardium. These problems are due to the convective losses of the agents to the systemic circulation. By going rapidly across the capillary wall, the small molecules are rapidly carried away by the bloodstream. Local delivery of an easily transported molecule is difficult because local delivery concentrations are rapidly reduced at very small distances from the delivery site due to convective losses. Such easily transported agents cannot treat an effective area of tissue locally without raising the systemic concentrations of the agents to a therapeutic level.

SUMMARY

The therapeutic compounds described below comprise very small capsules which can be injected into body tissue, particularly the heart. The capsules include an encapsulating layer which surrounds a therapeutic agent. After injection, the encapsulating layer degrades or dissolves, and the therapeutic agent is released within the heart. The therapeutic agent may be one of any number of known agents such as anti-arrhythmic drugs, gene therapy solution, and macromolecules intended to have either acute or long term effects on the heart. While some of these therapeutic agents are used to treat the heart by injecting them into the heart, they are of such small size that they readily enter the cardiac capillary system and the cardiac lymphatic system, and are quickly transported away from the injection site. Thus, in prior treatment methods, relatively large doses and repeated doses are required to provide therapeutic effect at the injection site. To provide a solution to this problem, the capsules described below are provided in sizes that are too large to permit capillary transport or lymphatic transport. Thus, injected capsules are immobile within the heart tissue, and upon degradation they will release a therapeutic agent very near the site of injection. The capsules may also be provided in sizes that are too large to permit capillary transport, but small enough to enter the lymphatic system and be transported away from the injection site in the cardiac lymphatic system, so that the therapeutic effect is provided at some distance from the injection site. The encapsulating layer may be made from various materials including biodegradable polymers in the form of microspheres, or from standard vesicle forming lipids which form liposomes and micelles.

DETAILED DESCRIPTION OF THE INVENTION

Figure 1:
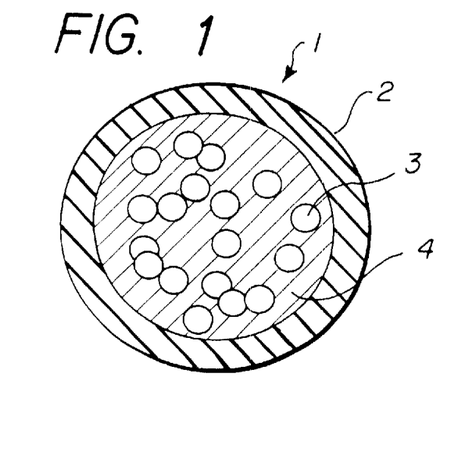
FIG. 1 illustrates an encapsulated therapeutic agent designed for injection into the heart.

FIG. 1 illustrates a microdrug delivery system which is comprised of a compound or substance for use in delivering a therapeutic agent to the heart. The compound is comprised of numerous capsules 1 which are made up of an encapsulating layer 2 which may form a microsphere formulated from Prolease™ or other biodegradable microsphere material, or from vesicle forming lipids which may form a liposome or micelle, and a therapeutic agent 3 within the encapsulating layer. Therapeutic agent may be imbedded in a biodegradable polymer, or in a carrier fluid 4. The encapsulating layer is typically pharmacologically inactive, although techniques to make it active to promote cellular uptake and/or receptor binding are known in the art. The therapeutic agent may be any of a wide variety of drugs and other compounds used for treatment of various ailments of the heart. The capsules are carried within a solution such as pH controlled saline to create a slurry which can be injected into the heart of a patient. Prior to injection, the encapsulating layer will protect the macromolecule from mechanical and chemical degradation within the catheter or needle used for injection. Once injected into the heart tissue, the size of the encapsulating layer will inhibit transport of the compound away from the injection site, either through the cardiac capillary system and/or the cardiac lymphatic system. Also once injected, the encapsulating layer will degrade, either due to chemical conditions, biological conditions, or temperature conditions within the heart wall, and release the encapsulated molecule. The time period over which the encapsulating layer degrades is variable, depending upon its formulation, such formulations being available in the art. The half life for degradation may be selected from several minutes to several days, depending on the therapy intended. Thus a sustained reservoir of therapeutic agent is created within the heart tissue near the injection site, and therapeutic agents are slowly released near the injection site to treat nearby tissue. The need to flood the entire heart and/or the entire blood system of the patient is eliminated, so that very small doses of therapeutic agents are necessary. This reduces the cost of treatment, and minimizes the otherwise harsh side effects associated with many effective therapeutic agents.

Figure 1A:
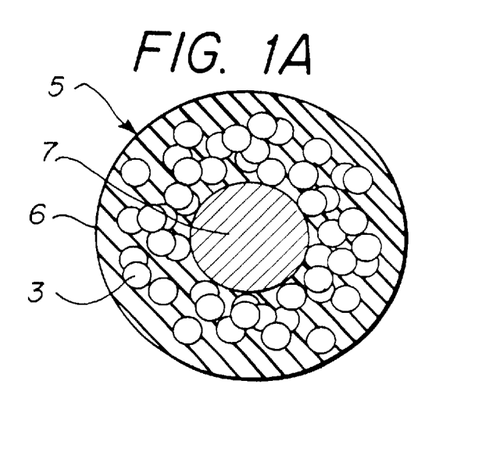
FIG. 1a illustrates an microsphere encapsulated therapeutic agent designed for injection into the heart.

FIG. 1a illustrates the formulation of the microdrug delivery system from a microsphere formulated from Prolease™, biodegradable polymers, or particulate controlled release matrix with molecules of therapeutic agent dispersed throughout the microsphere. The microsphere 5 in FIG. 1a includes numerous molecules or particles of therapeutic agents 3 dispersed throughout the solid biodegradable microsphere or particulate controlled release matrix 6. As the microsphere material degrades, therapeutic agents are slowly released from the microsphere. This formulation differs from the capsule formulation, but may be employed to achieve similar results. In one preferred embodiment, the core 7 of the solid biodegradable microsphere contains no therapeutic drug at a radius less then approximately 10 μm, preferably about 7.5 μm. Thus the core of the microsphere, to a radius of up to 10 μm, preferably 7.5 μm, may be devoid of therapeutic agent. This prevents problems associated with migration of the potentially potent depot within the lymphatic system. The core of the microsphere may also be designed to have a longer degradation half life so that essentially all of the drug will be delivered before the microsphere can substantially migrate through the lymphatic networks. Thus, the particulate micro delivery systems includes millispheres, microspheres, nanospheres, nanoparticles, liposomes and micelles, cellular material and other small particulate controlled release structures which can be advanced in a fluid suspension or slurry and be delivered to a depth within the heart muscle. These small drug delivery systems may deliver therapeutic agents as diverse as small molecule antiarrhythmics, agents that promote angiogenesis, and agents that inhibit restenosis. They may also be combined in cocktails with steroid agents such as dexamethasome sodium phosphate to prevent inflammatory response to the implanted materials. Separate particulate drug delivery systems for delivering different agents to the same region of the heart may also be used. The release kinetics of separate micro delivery systems may also be different.

Delivery of small drug delivery systems reduce the likelihood of causing embolic events in the in the brain, kidneys, or other organs should these drug delivery systems escape into the left chambers of the heart. Because the systems are small only very small arterioles would be occluded should one of them escape into the blood within the left chambers of the heart. This is not a problem in the right side of the heart, as the lungs act as a filter of potentially embolic materials.

Figure 2:
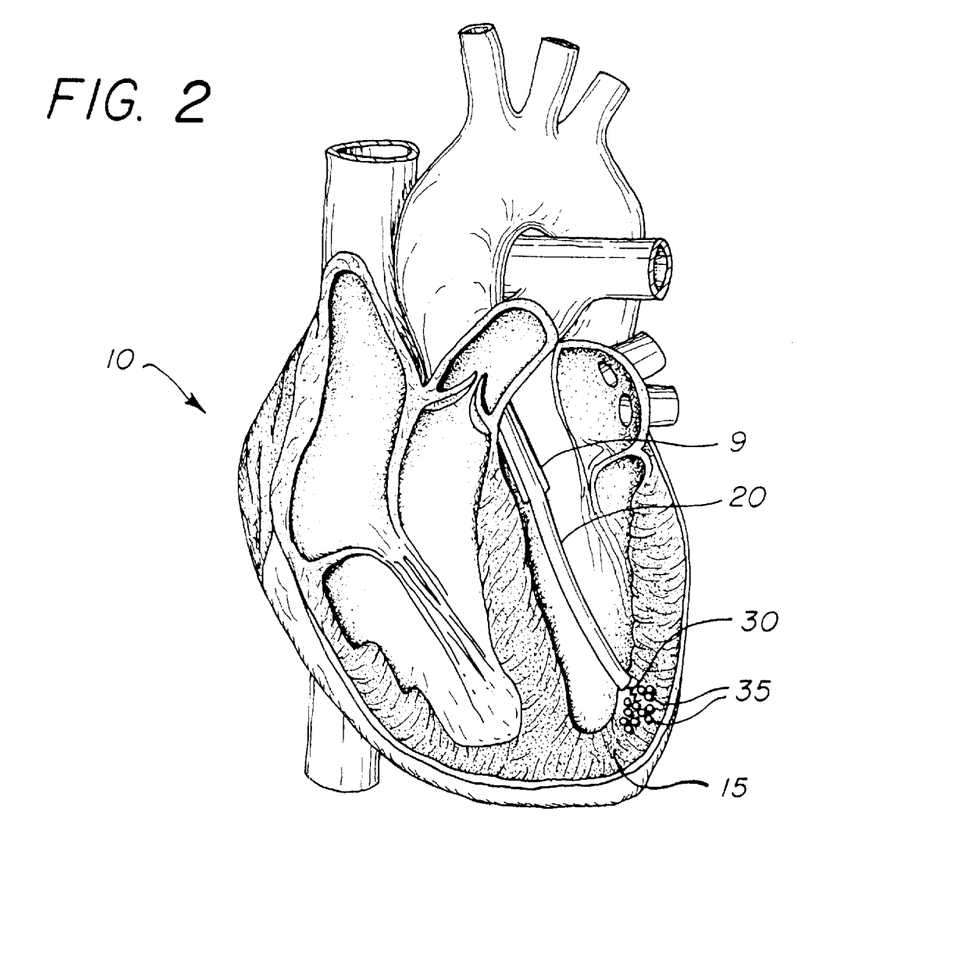
FIG. 2 illustrates a method for injection of therapeutic agents into the heart.

FIG. 2 shows a catheter system 9 with centrally located drug delivery catheter 20 implanted at a depth within the left ventricular apex 15. Hollow penetrating structure 30 has penetrated the heart muscle, and has transported particulate encapsulated agents 35 such as VEGF, bFGF, or other therapeutic agent to a depth within the heart muscle. The encapsulated agents are injected into the heart muscle (the myocardium) in an intact portion of the heart muscle (that is, not into a vessel such as the ventricle chamber, a coronary artery or a TMR channel which are subject to blood flow and immediate transport of the injected particles from the area). The capsules or microspheres are suspended within a fluid inside the catheter to facilitate injection. The use of small drug delivery systems in slurry or suspension delivered by a fluidic pathway (a needle or catheter) to a depth within the myocardium can solve different problems in pharmacokinetics of local cardiovascular drug delivery. Such an approach can provide for well controlled and easily administered sustained dosage of therapeutic macromolecules, eliminate the issue of convective losses of small molecules for local delivery, and increase the ability of gene therapy preparations to gain access through the cell membrane.

Problems exist for macromolecular therapies in the heart such as short half lives and the presence of endogenous inhibitors. Many macromolecular therapies may be improved by providing a sustained dosage over time to overcome endogenous inhibitors, as well as encapsulation to protect the macromolecule from degradation.

The interstitial (intramuscular or intra-myocardial) delivery of particulate drug delivery systems for sustained release such as biodegradable microspheres solves these problems. Particulate systems, such as microspheres, enable the time course of delivery and area of treatment to be controlled. In addition, such particulate systems may be delivered to the target site by a fluid pathway within a drug delivery catheter such as those described in the prior art. The advantages of these particulate delivery systems is that they are implanted at a depth within the heart tissue and the implanted catheter device can be removed immediately. Thus, a very quick procedure may be performed on an outpatient basis to deliver particulate drug delivery systems to a depth within a patient's heart for sustained delivery measured in days to weeks.

The microspheres to be used in this treatment are manufactured to be large enough to prevent migration within the myocardial interstitium, but also small enough to be deliverable by a catheter fluid pathway to a depth with the myocardium. Microspheres such as Alkerme's (Cambridge, Mass.) Prolease system enables freeze dried protein powder to be homogenized in organic solvent and sprayed to manufacture microspheres in the range of 20 to 90 µm (microns). Development of such microsphere depots for sustained release of proteins with unaltered integrity requires methods to maintain stability during purification, storage, during encapsulation, and after administration. Many of these techniques have been recently summarized in the literature. See, e.g., Scott D. Putney, and Paul A. Burke: Improving protein therapeutics with sustained release formulations, Nature Biotechnology, Volume 16, February 1998, 153–157. Issues associated with degradation for biodegradable polymers used in such microspheres are also well known [Robert Miller, John Brady, and Duane E. Cutright: Degradation Rates of Oral Resorbabale Implants {Polylactates and Polyglycolates}: Rate Modification and Changes in PLA/PGA Copolymer Ratios, J. Biomed. Mater. Res., Vol. II, PP. 711–719 (1977). The value of delivering microsphere encapsulated macromolecular agents such as proteins bFGF and VEGF to a depth within the heart muscle for controlled release have not been described, and have substantial unrecognized benefits over other delivery approaches.

Figure 3:
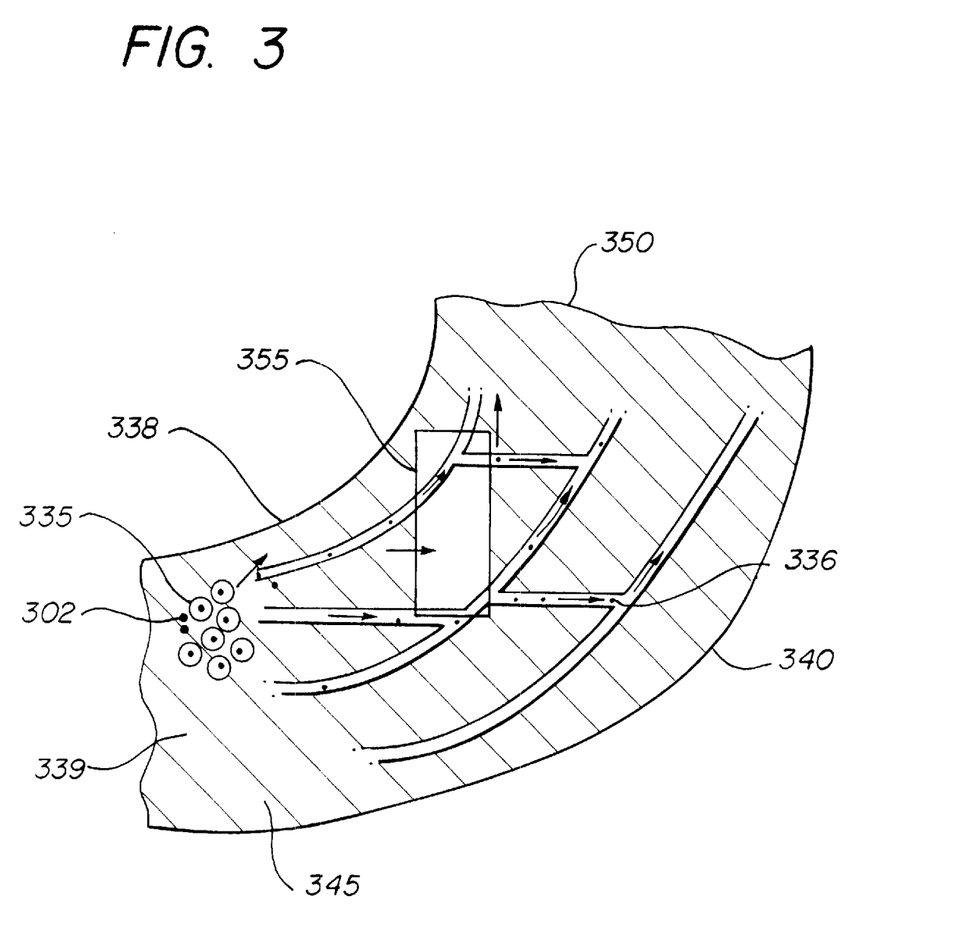
FIG. 3 illustrates the expected transportation of molecules released from degrading microspheres injected within the myocardium.

FIG. 3 shows a schematic description of microsphere encapsulated agents for delivery. Macromolecule angiogenic agents 336 such as VEGF and bFGF are delivered with biodegradable microspheres 335 in combination with biodegradable microspheres 302 enclosing dexamethasone sodium phosphate or other anti inflammatory steroid. In other embodiments the anti-inflamatory agents may be combined with a particular therapeutic within the same encapsulation. The microspheres are injected through the endocardium 338 and into the myocardium 339 so that they reside interstitially within the heart tissue. Both microspheres 335 and 302 are too large to be transported away by either the capillary system or the lymphatic system from the injection site within the myocardium. Where the microspheres are greater than about 15 micrometers in diameter, they will remain at the injection site and will not migrate. Where the microspheres have a diameter less than about 1 micrometer nanometers, they will migrate in the cardiac lymphatic system, but will not enter the cardiac capillary system. As the microspheres degrade over time, their components and the therapeutic molecules will be transported away from the injection site by the myocardial lymphatic system which has been described in relation to the transport of extravasated proteins from the endocardium 338 to the epicardium 340, and from the apex of the heart 345 towards the base of the heart 350. [Albert J. Miller, Lymphatics of the Heart, Raven Press, New York, 1982.] Here the microspheres are delivered endocardially and inferiorly (that is, upstream in the lymphatic system) to the region to be treated, identified here schematically by window 355. Clearly regions within window 355 and regions directly adjacent to the window will all result in effective delivery of agents to the desired target, and are viable approaches as well. The large molecules delivered in such a fashion will be transported through the lymphatics far more slowly than small molecules which would be more rapidly convected away from the delivery region by the blood supply. But approaches exist to minimize the issues associated with convective losses of small molecules.

The method of packaging the small molecule so that it cannot be convected away by the blood, yet will be distributed locally in the tissue, and then effecting its action on the tissue can be accomplished with liposomal encapsulation. The term "liposome" refers to an approximately spherically shaped bilayer structure, or vesicle, comprised of a natural or synthetic phospholipid membrane or membranes, and sometimes other membrane components such as cholesterol and protein, which can act as a physical reservoir for drugs. These drugs may be sequestered in the liposome membrane or may be encapsulated in the aqueous interior of the vesicle. Liposomes are characterized according to size and number of membrane bilayers. Vesicle diameters can be large (>200 nm) or small (<50 nm) and the bilayer can have unilamellar, oligolamellar, or multilamellar membrane.

Liposomes are formed from standard vesicle forming lipids, which generally include neutral and negatively charged phospholipids with or without a sterol, such as cholesterol. The selection of lipids is generally guided by considerations of liposome size and ease of liposome sizing, and lipid and water soluble drug release rates from the site of liposome delivery. Typically, the major phospholipid components in the liposomes are phosphatidylcholine (PC), phosphatidylglycerol (PG), phosphatidyl serine (PS), phosphatidylinositol (PI) or egg yolk lecithin (EYL). PC, PG, PS, and PI having a variety of acyl chains groups or varying chain lengths are commercially available, or may be isolated or synthesized by known techniques. The degree of saturation can be important since hydrogenated PL (HPL) components have greater stiffness than do unhydrogenated PL components; this means that liposomes made with HPL components will be more rigid. In addition, less saturated Pls are more easily extruded, which can be a desirable property particularly when liposomes must be sized below 300 nm.

Current methods of drug delivery by liposomes require that the liposome carrier will ultimately become permeable and release the encapsulated drug. This can be accomplished in a passive manner in which the liposome membrane degrades over time through the action of agents in the body. Every liposome composition will have a characteristic half-life in the circulation or at other sites in the body. In contrast to passive drug release, active drug release involves using an agent to induce a permeability change in the liposome vesicle. In addition, liposome membranes can be made which become destabilized when the environment becomes destabilized near the liposome membrane (Proc. Nat. Acad. Sci. 84, 7851 (1987); Biochemistry 28: 9508, (1989).) For example, when liposomes are endocytosed by a target cell they can be routed to acidic endosomes which will destabilize the liposomes and result in drug release. Alternatively, the liposome membrane can be chemically modified such that an enzyme is placed as a coating on the membrane which slowly destabilizes the liposome (The FASEB Journal, 4:2544 (1990). It is also well known that lipid components of liposomes promote peroxidative and free radical reactions which cause progressive degradation of the liposomes, and has been described in U.S. Pat. No. 4,797, 285. The extent of free radical damage can be reduced by the addition of a protective agent such as a lipophilic free radical quencher is added to the lipid components in preparing the liposomes. Such protectors of liposome are also described in U.S. Pat. No. 5,190,761, which also describes methods and references for standard liposome preparation and sizing by a number of techniques. Protectors of liposomal integrity will increase the time course of delivery and provide for increased transit time within the target tissue.

Liposomal encapsulation of small molecules makes local delivery possible. By having a liposomal preparation which is unstable in the body, it will collapse after it is delivered. Liposomes can be constructed in varying size, including the size range less than 400 nm, preferably 200–250 nm. Between the time of delivery and the time of collapse, the liposomes in the size range less than 400 nm will be transported into and through the lymphatics and provide for redistribution of small molecules. Delivery of liposomes that degrade rapidly once delivered to the body in a matter of minutes goes against the typical approaches for liposomal delivery and design. Typically pH sensitive liposomes involves the destabilization of the liposome in the endosome as the pH falls from physiological 7.4 to 5.0, while here we are describing liposomes which become destabilized near pH 7.4. [Chun-Jung Chu and Francis C. Szoka: pH Sensitive Liposomes, Journal of Liposome Research, 4(1), 361–395 (1994)].

Figure 4A:
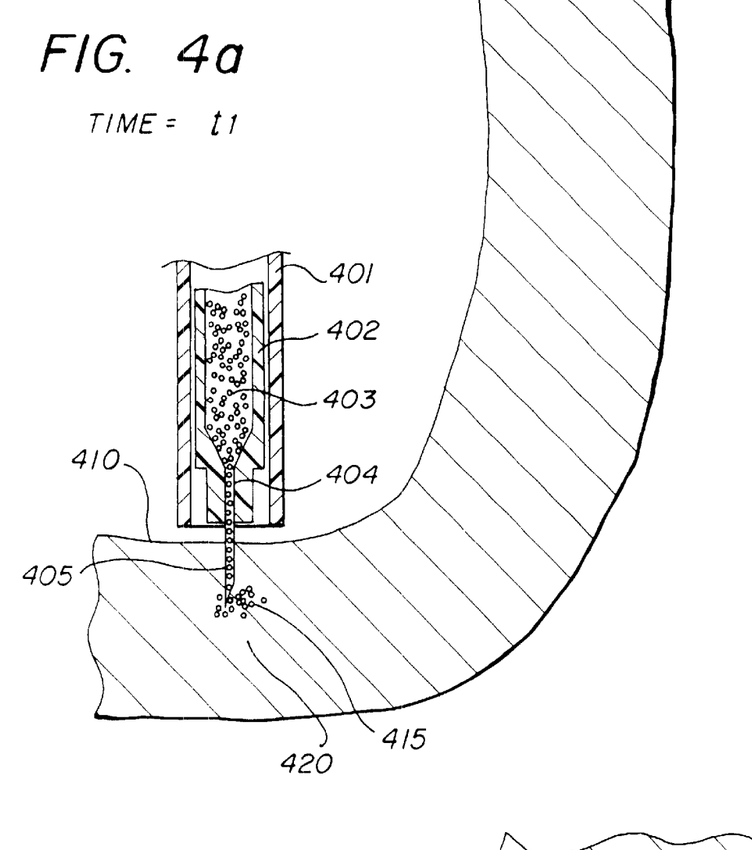
FIGS. 4a through 4d illustrate the progression of injected liposome encapsulated small molecules within the heart tissue after injection.
Figure 4B:
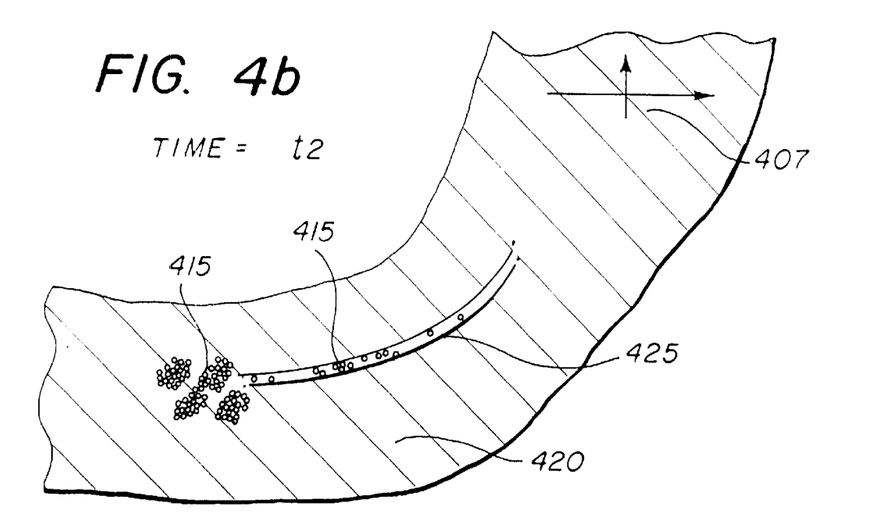
Figure 4C:
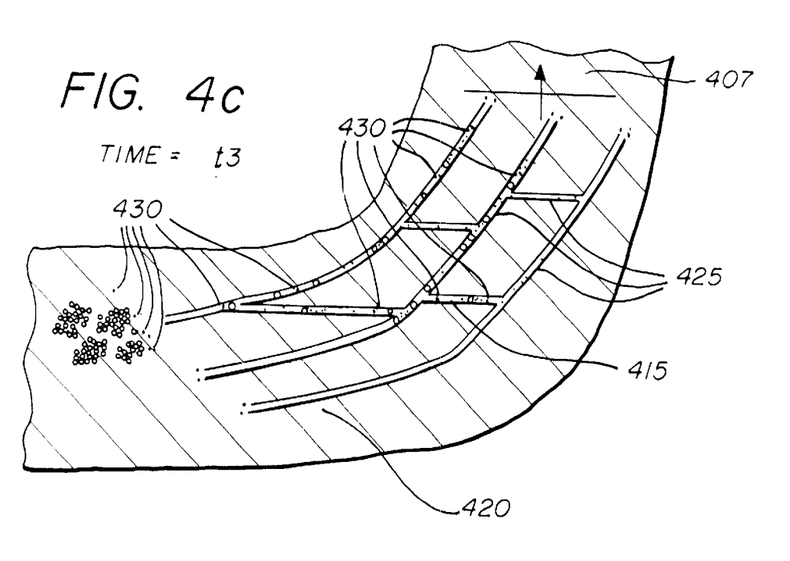
Figure 4D:
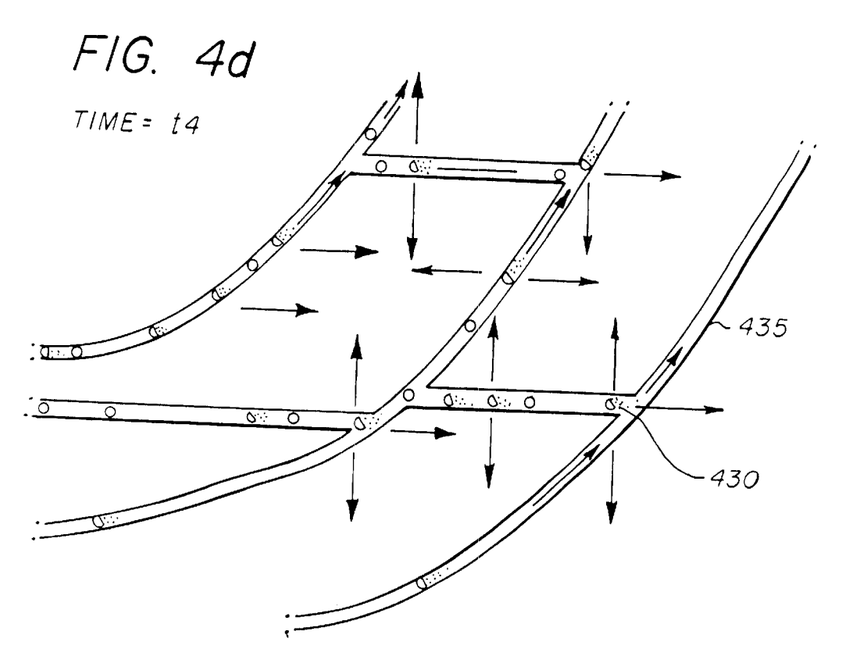

FIG. 4a shows a schematic of the delivery of small molecules within liposomes which are unstable at physiological pH (the pH of the heart tissue or the physiological environment into which the molecules are delivered). A guiding catheter 401 is shown with a single lumen needle drug delivery catheter 402 containing liposome encapsulated small molecules 403 which are delivered through needle 404 by way of needle fitting 404. Here the penetrating needle 405, crosses the endocardium 410 to deliver liposomes 415 to a depth within the heart wall 420. Although the liposomes could be various sizes and have a number of lipid bilayers, in the preferred embodiment they are small unilamellar liposome vesicles (SUVs) to augment their rapid uptake by the cardiac lymphatic system. The drug delivery catheter 402 contains liposomes bathed in a solution at their stable pH so that they do not collapse prematurely. FIG. 4b shows that the catheter has been removed and that the uptake of the SUVs 415 by a lymphatic vessel 425 at some time t2 later than the time they were delivered t1 to the myocardial interstitium, such as the subendocardial interstitium. Of course, other physiochemical properties could be used such that the liposomal preparations are delivered from a system in which they are stable to a system at a depth within the heart with different physio-chemical properties in which they are unstable. Temperature is another possible property that could be varied. Arrows near 407 show that lymphatic transport is from endocardium to epicardium and from apex to base in the heart. The lymphatic transport will carry the encapsulated small molecules a distance which will be governed by their stability and mean time to liposomal degradation. FIG. 4c shows the same tissue in a larger view at time t3 later than time t2 in which SUVs 415 are degrading and releasing small molecule drugs 430 within the lymphatics. The spread of the released drug in the degraded liposomes 430 provides therapeutic treatment to a large region of heart tissue while systemic effects are minimized. FIG. 4d shows that upon degradation, the small molecules 430 will be transported through the lymphatic vessel wall 435 to the adjacent myocytes, and be convected rapidly away from the region. This transport through the lymphatic walls is shown schematically by the large arrows at the site of the degraded liposome with released small molecules. Because of the inability of the small molecules to be convected away rapidly until the liposome collapses, a much larger region of tissue will be able to be treated locally than by local infusion of the small molecules themselves. In one embodiment, oleic acid (OA) and dioleoylphosphatidylethanolamine (DOPE) devoid of cholesterol which have been shown to be extremely unstable in the presence of body fluid plasma [Liu, D. and Huang, L., Role Of Cholesterol In The Stability Of Ph Sensitive, Large Unilamellar Liposomes Prepared By The Detergent-Dialysis Method, Biochim Biophys. Act, 981, 254–260 (1989)] and could be used to encapsulate small molecule gene regulators such as hormones or antiarrhythmic agents.

In another embodiment, liposomes of dimyristoylphosphatidylcholine (DMPC) or dipalmitoylphosphatidylcholine (DPPC), cholesterol (CHOL) and dicetylphosphate (DCP) containing Amiodarone are prepared at pH 4.5 using DMPC:CHOL:DCP (3:1:2mol ratio) and are stable at this pH, and are less stable at the neutral pH of the heart. Because the stability of the liposome can be varied, and even triggered by external inputs, a specific size of tissue may be treated locally with small molecules in this fashion.

If the small molecule has a very short half-life, or antagonists have been delivered systematically to prevent the drug from having systemic effects, such an approach will enable local delivery of small molecules to regions of varying sizes within the myocardium. Alternatively, some small molecules may be delivered transiently only when needed, such as to terminate a cardiac arrhythmia, and so that systemic effects are minimized. Such systems could involve a permanently implantable infusion system for either continuous or transient local delivery as has been described in the art.

Liposomal encapsulated agents delivered to the myocardium will also provide advantages to other therapeutic agents. Liposomal encapsulation can improve transfection of gene therapy preparations, and cytosolic delivery of macromolecules. Liposomal delivery systems can be used to alter macromolecule and gene therapy pharmacokinetics and improve their ability to enter the cell cytosol. Delivery vehicles capable of delivering agents to the cell cytosol have been created in fusogenic liposomes, which enable them to cross the cell membrane in a lipophilic vesicle. Newer techniques for triggering the liposomes so that their contents may be released within the cytosol have been developed, and a brief review of this work has appeared in the literature [Oleg Gerasimov, Yuanjin Rui, and David Thompson, "Triggered release from liposomes mediated by physically and chemically induced phase transitions", in Vesicles, edited by Morton Rosoff, Marcel Dekker, Inc., New York, 1996.] Because the liposome is not stable at the physicochemical conditions within the body, it can be designed to degrade in a time period less than it takes to get to the cardiac lymph node. Once the liposome is degraded, the body can address the liposomal contents and break them up. Liposomes within the systemic circulation can then be minimized, as will endocytosis of the macromolecules and gene therapy preparations outside the target region. No approach for delivering such liposomal encapsulated agents to a depth within the myocardium has been described.

As described, the endocardial to epicardial, and apex to base lymphatic transport pathways can be used to deliver macromolecules and particulate drug delivery systems to the targeted region in need of therapy. The increased risk of ischemia in the subendocardium implies that it is the tissue in need of therapeutic intervention. This has been hypothesised as being due to the higher interstitial pressures during cardiac systole, which may limit perfusion of this tissue region as opposed to subepicardial tissue. In order to treat this region with therapeutic agents from a locally delivered depot site, delivery should be such that endogenous transport pathways deliver agents to the target regions. This can be accomplished by delivering agents on the endocardial side of the ischemic zone, and towards the apex of the heart. Such an approach has not been previously described. The internal lymphatic system of the heart can also be used to control delivery of the therapeutic agents throughout the heart. For example, liposome encapsulated or micelle encapsulated amiodarone, or other anti-arrhythmic agents can be injected into the ventricle wall, (and the liposomes formulated for a half life of about five minutes to sixty minutes), whereupon the lymphatic system will transport the liposomes upward toward the atrium of the heart to the vicinity of the cardiac lymph node. The cardiac lymph node is closely proximate the atrium of the heart, so that by natural lymphatic action, the compound injected into the ventricle wall transported into the atrial wall. This transport happens within minutes, so that the release of the therapeutic molecules will occur in the walls of the atrium. This has potential for treating atrial arrhythmias. (Thus it can be appreciated that variation of the size of the encapsulated therapeutic agent can be employed in remarkable new therapies.)

The agents to be delivered may include small molecules, macromolecules, and gene therapy preparations. These will be briefly defined.

"Small molecules" may be any smaller therapeutic molecule, known or unknown. Examples of known small molecules relative to cardiac delivery include the antiarrhythmic agents that affect cardiac excitation. Drugs that predominantly affect slow pathway conduction include digitalis, calcium channel blockers, and beta blockers. Drugs that predominantly prolong refractoriness, or time before a heart cell can be activated, produce conduction block in either the fast pathway or in accessory AV connections including the class IA antiarrhythmic agents (quinidine, procainimide, and disopyrimide) or class IC drugs (flecainide and propefenone). The class III antiarrhythmic agents (sotolol or amiodorone) prolong refractoriness and delay or block conduction over fast or slow pathways as well as in accessory AV connections. Temporary blockade of slow pathway conduction usually can be achieved by intravenous administration of adenosine or verapamil. [Scheinman, Melvin: Supraventricular Tachycardia: Drug Therapy Versus Catheter Ablation, Clinical Cardiology Vol 17, Suppl. II 11-II-15 (1994)]. Many other small molecule agents are possible, such as poisonous or toxic agents designed to damage tissue that have substantial benefits when used locally such as on a tumor. One example of such a small molecule to treat tumors is doxarubicin.

A "macromolecule" is any large molecule and includes proteins, nucleic acids, and carbohydrates. Examples of such macromolecules include the growth factors, Vascular Endothelial Growth Factor, basic Fibroblastic Growth Factor, and acidic Fibroblastic Growth Factor, although others are possible. Examples of macromolecular agents of interest for local delivery to tumors include angiostatin, endostatin, and other anti-angiogenic agents.

A "gene therapy preparation" is broadly defined as including genetic materials, endogenous cells previously modified to express certain proteins, exogenous cells capable of expressing certain proteins, or exogenous cells encapsulated in a semi-permeable micro device. This terminology is stretched beyond its traditional usage to include encapsulated cellular materials as many of the same issues of interstitial delivery of macrostructures apply.

The term "genetic material" generally refers to DNA which codes for a protein, but also encompasses RNA when used with an RNA virus or other vector based upon RNA. Transformation is the process by which cells have incorporated an exogenous gene by direct infection, transfection, or other means of uptake. The term "vector" is well understood and is synonymous with "cloning vehicle". A vector is non-chromosomal double stranded DNA comprising an intact replicon such that the vector is replicated when placed within a unicellular organism, for example by a process of transformation. Viral vectors include retroviruses, adenoviruses, herpesvirus, papovirus, or otherwise modified naturally occurring viruses. Vector also means a formulation of DNA with a chemical or substance which allows uptake by cells. In addition, materials could be delivered to inhibit the expression of a gene. Approaches include: antisense agents such as synthetic oligonucleotides which are complimentary to RNA or the use of plasmids expressing the reverse compliment of a gene, catalytic RNA's or ribozymes which can specifically degrade RNA sequences, by preparing mutant transcripts lacking a domain for activation, or over express recombinant proteins which antagonize the expression or function of other activities. Advances in biochemistry and molecular biology in recent years have led to the construction of recombinant vectors in which, for example, retroviruses and plasmids are made to contain exogenous RNA or DNA respectively. In particular instances the recombinant vector can include heterologous RNA or DNA by which is meant RNA or DNA which codes for a polypeptide not produced by the organism susceptible to transformation by the recombinant vector. The production of recombinant RNA and DNA vectors is well understood and need not be described in detail.

Many delivery systems could be used to deliver these agents to a region of the myocardial interstitium. During surgical procedures, a syringe may suffice, but it is more likely that a transvascular delivery catheter such has been called out would be used to deliver the appropriate therapeutic agents to the appropriate sites. Essentially, a steerable catheter would be advanced to a location within the heart chamber and placed adjacent to the heart wall. The drug delivery catheter would be advanced so that it penetrates the heart wall and the desired volume of particulate delivery slurry or suspension (0.05 ml to 2.0 ml) would be infused. The penetrating structure would be disengaged, and the drug delivery catheter would be pulled back a short distance within the delivery catheter. The steerable catheter would be reposition, and the process may be repeated a number of times if so desired.

The benefits of the different controlled systems may also be combined. For example, to provide for local small molecule delivery that is sustained over time, and does not require an indwelling drug delivery system in the heart chamber, the SUV liposomes containing the small molecules could be delivered within biodegradable microdrug delivery systems such as larger more stable liposomes or other fully encapsulated controlled release system, such as a biodegradable impermeable polymer coatings. The time course of release is governed then by the additive time delay of the barriers that separate the therapeutic agent from the host, as well as their combined transport pathways. Microsphere delivery systems could also be used.

While the inventions have been described in relation to the treatment of cardiac tissue, it should be appreciated that the compounds and methods of treatment may be applied to various body tissues. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method of delivering a therapeutic molecule to myocardial interstitium to achieve local therapy to the heart muscle, said method comprising the steps of:

encasing the therapeutic molecule within a liposome, the liposome having a half-life within mammal myocardial tissue of less than about thirty minutes; and injecting the liposome into the myocardial interstitium.

2. The method of claim 1 wherein the injecting step comprises providing a catheter system that delivers the stable liposomal preparation through an endocardial hollow penetrating delivery system.

3. The method of claim 1 wherein the injecting step comprises an epicardial injection.

4. The method of claim 1 wherein the therapeutic molecule is a small molecule with a molecular weight less than about 2000 daltons.

5. The method of claim 1 wherein the therapeutic molecule is a macromolecule.

6. The method of claim 1 wherein the therapeutic molecule is a gene therapy preparation.

7. A method of delivering a therapeutic agent to myocardium comprising the steps of:

providing a liposomal delivery catheter with a fluid lumen, the fluid lumen having a different physico-chemical state than the mammal myocardium; and injecting liposomes into said myocardium, the liposomes being stable in the fluid lumen and unstable in the mammal myocardium.

8. A method of delivering therapeutic macromolecules locally to the myocardial interstitium to achieve local therapy to the heart muscle, said method comprising the steps of: encasing the macromolecules within an intact controlled release particle between 15 and 150 micrometers in diameter; and injecting the controlled release particle into the myocardial interstitium.

9. The method of claim 8 wherein the injecting step comprises providing a catheter system that delivers the controlled release particle through an endocardial hollow penetrating delivery system.

10. A method of treating the heart of a patient by injecting a therapeutic agent into the tissue of the heart, said method comprising the step of:

forming a plurality of capsules by encapsulating molecules of the therapeutic agent within an encapsulating layer, said encapsulating layer being degradable within the heart tissue, said capsules being of sufficient size to prevent capillary transport of the capsules after injection into the heart tissue;

injecting the capsules into the heart tissue;

allowing the encapsulating layer to degrade within the heart tissue and thereby release molecules of therapeutic agent within the heart tissue.

11. The method of claim 10 further comprising the steps of:

formulating the capsules so that they are stable in a storage environment and unstable in a physiological environment, and storing the capsules in the storage environment prior to injection into the heart tissue.

12. The method of claim 10 wherein:

the encapsulating layer comprises a liposome.

13. The method of claim 10 wherein:

the encapsulating layer comprises a micelle.

14. The method of claim 10 wherein:

the encapsulating layer comprises a liposome having a diameter in the range of about 50 nm to about 400 nm the therapeutic agents comprise at least one of:

macromolecules, gene therapy preparations, antiarrhythmic agents.

15. The method of claim 10 further comprising:

determining a site of intended treatment within the heart tissue;

injecting the capsules into the heart tissue at a point upstream in the lymphatic system relative to an area of intended treatment.

16. The method of claim 10 wherein the capsules are of sufficient size to prevent lymphatic transport of the capsule after injection into the heart tissue.

17. A substance for treatment of body tissue comprising:

a plurality of capsules comprising an encapsulating layer and a therapeutic agent within the encapsulating layer, wherein said encapsulating layer is degradable when injected into the body tissue; the half life of said encapsulating layers being between five and sixty minutes;

said capsules having an outer diameter less than about 400 nanometers;

said therapeutic agent having a pharmacological effect on the body tissue upon degradation of the encapsulating layer.

18. The substance of claim 17 wherein the capsules further comprise a core of about 7.5 $\mu$m diameter which is substantially devoid of therapeutic agent.

19. A substance for treatment of body tissue comprising:

a plurality of capsules comprising an encapsulating layer and a therapeutic agent within the encapsulating layer, wherein said encapsulating layer is degradable when injected into the body tissue;

said capsules having an outer diameter between about 15 and 150 microns, the capsules also having a core of about 7.5 $\mu$m diameter which is substantially devoid of therapeutic agent;

said therapeutic agent having a pharmacological effect on the body tissue upon degradation of the encapsulating layer.

20. A substance for treatment of body tissue comprising:

a plurality of microspheres comprising an outer layer and an inner core, the outer layer incorporating a therapeutic agent, the inner core comprising a substantially inert agent, the outer layer being degradable when injected into the body tissue thereby releasing the therapeutic agent to the body tissue;

said therapeutic agent having a pharmacological effect on the body tissue.

* * * * *